(12) United States Patent
Kasako

(10) Patent No.: US 9,165,119 B2
(45) Date of Patent: Oct. 20, 2015

(54) POWER INJECTOR WITH KEEP VEIN OPEN FUNCTIONALITY

(75) Inventor: Andrew H. Kasako, Springdale, OH (US)

(73) Assignee: LIEBEL-FLARSHEIM COMPANY LLC, Hazelwood, MO (US)

( * ) Notice: Subject to any disclaimer, the term of this patent is extended or adjusted under 35 U.S.C. 154(b) by 0 days.

(21) Appl. No.: 12/996,989

(22) PCT Filed: Aug. 25, 2009

(86) PCT No.: PCT/US2009/054827
§ 371 (c)(1),
(2), (4) Date: Dec. 9, 2010

(87) PCT Pub. No.: WO2010/027757
PCT Pub. Date: Mar. 11, 2010

(65) Prior Publication Data
US 2011/0137161 A1    Jun. 9, 2011

Related U.S. Application Data

(60) Provisional application No. 61/091,751, filed on Aug. 26, 2008.

(51) Int. Cl.
| | |
|---|---|
| *G06F 19/00* | (2011.01) |
| *A61M 5/145* | (2006.01) |
| *A61M 5/14* | (2006.01) |
| *A61B 6/00* | (2006.01) |
| *A61M 5/00* | (2006.01) |
| *A61M 5/142* | (2006.01) |

(52) U.S. Cl.
CPC ....... *G06F 19/3468* (2013.01); *A61M 5/14546* (2013.01); *A61B 6/548* (2013.01); *A61M 5/007* (2013.01); *A61M 2005/1404* (2013.01); *A61M 2005/14208* (2013.01); *A61M 2005/14553* (2013.01); *G06F 19/321* (2013.01)

(58) Field of Classification Search
CPC ........... A61M 2005/1404; A61M 2005/14208; A61M 5/007
USPC ........................................................ 600/432
See application file for complete search history.

(56) References Cited

U.S. PATENT DOCUMENTS 5,056,992 A * 10/1991 Simons et al. ................ 417/474
5,153,827 A    10/1992 Coutré et al.
(Continued)

FOREIGN PATENT DOCUMENTS

JP    2001-037875 A    2/2001

*Primary Examiner* — Unsu Jung
*Assistant Examiner* — Saurel J Selkin
(74) *Attorney, Agent, or Firm* — Marsh Fischmann & Breyfogle LLP

(57) ABSTRACT

Disclosed are systems and methods for power injectors incorporating a keep vein open functionality that is operable when an injection protocol (112) is suspended. The injector includes control logic (110) configured to include the injection protocol (112), and a separate drip mode injection protocol (114) executable only during a suspension of the injection protocol (112). In one embodiment, the drip mode injection protocol (114) is automatically or manually initiated immediately after and in response to the suspension of the injection protocol (112). In another embodiment, the drip mode injection protocol (114) is automatically initiated after a predetermined delay from start of the suspension of the injection protocol (112). The configuration parameters for the drip mode injection protocol (114) may be programmable prior to the initiation of an injection procedure, immediately prior to the execution of the drip mode injection protocol (114), or hard-coded into the injector.

15 Claims, 10 Drawing Sheets

(56) References Cited

U.S. PATENT DOCUMENTS 5,429,602 A 7/1995 Hauser
2002/0216643 11/2003 Zatezalo et al.
2003/0216643 A1 11/2003 Zatezalo et al.
2005/0203389 A1 9/2005 Williams

* cited by examiner

POWER INJECTOR WITH KEEP VEIN OPEN FUNCTIONALITY

RELATED APPLICATIONS

This application is a U.S. National Stage of PCT/US2009/054827, filed on 25 Aug. 2009, which claims priority to U.S. Provisional Patent Application No. 61/091,751, filed on 26 Aug. 2008, and entitled "POWER INJECTOR WITH KEEP VEIN OPEN FUNCTIONALITY".

FIELD OF THE INVENTION

The present invention generally relates to the field of power injectors and, more particularly, to power injectors that incorporate a keep vein open functionality that is operable when an injection protocol has been suspended.

BACKGROUND

Various medical procedures require that one or more medical fluids be injected into the patient. Medical imaging procedures oftentimes involve the injection of a contrast media into the patient, possibly along with saline or other fluids. Other medical procedures involve injecting one or more fluids into a patient for therapeutic purposes. Power injectors may be used for these types of applications.

A power injector generally includes what is commonly referred to as a powerhead. One or more syringes may be mounted to the powerhead in various manners (e.g., detachably; rear-loading; front-loading; side-loading). Each syringe typically includes what may be characterized as a syringe plunger, piston, or the like. Each such syringe plunger is designed to interface with (e.g., contact and/or temporarily interconnect with) an appropriate syringe plunger driver that is incorporated into the powerhead, such that operation of the syringe plunger driver axially advances the associated syringe plunger inside and relative to a barrel of the syringe. One typical syringe plunger driver is in the form of a ram that is mounted on a threaded lead or drive screw. Rotation of the drive screw in one rotational direction advances the associated ram in one axial direction, while rotation of the drive screw in the opposite rotational direction advances the associated ram in the opposite axial direction.

The operation of a power injector may be dictated by control logic. An injection protocol may be incorporated by the control logic to control the injection of one or more fluids into a patient. For example, an injection protocol may be defined by one or more phases, where each phase involves the injection of a programmed volume of a certain fluid into the patient at a programmed flow rate. One or more fluids may be used by an injection protocol, such as contrast media and saline. At least some injection protocols alternate between contrast media and saline injections.

SUMMARY

A first aspect of the present invention is embodied by a power injector that includes a syringe plunger driver and power injector control logic, where the syringe plunger driver includes a motorized drive source. The power injector control logic includes an injection protocol and a drip mode injection protocol. The drip mode injection protocol may be executed during a suspension of the injection protocol. That is, the power injector control logic may be configured to execute the drip mode injection protocol at a time when the injection protocol has been suspended.

A number of feature refinements and additional features are applicable to the first aspect of the present invention. These feature refinements and additional features may be used individually or in any combination. The following discussion is applicable to the first aspect, up to the start of the discussion of a second aspect of the present invention.

The power injector control logic may include a logic operator that is configured to transfer control from the injection protocol to the drip mode injection protocol upon an occurrence of a first condition. In one embodiment, the logic operator includes one or more instructions implemented in software. In other embodiments, the logic operator is implemented in hardware, or a combination or hardware and software. In one embodiment, the first condition includes a suspension of the injection protocol. In another embodiment, the first condition includes the passing of a time period after an initiation of and/or a beginning of the suspension of the injection protocol. In yet another embodiment, the first condition includes a manual interaction by an operator of the power injector.

A second aspect of the present invention is embodied by a power injector that includes a syringe plunger driver and power injector control logic. The syringe plunger driver includes a motorized drive source, while the power injector control logic includes an injection protocol, a drip mode injection protocol, and a logic operator. The logic operator is configured to transfer control from the injection protocol to the drip mode injection protocol upon an occurrence of a first condition.

A third aspect of the present invention is embodied by a power injector that includes a syringe plunger driver and power injector control logic. The syringe plunger driver includes a motorized drive source, while the power injector control logic includes an injection protocol, a drip mode injection protocol, and a drip mode injection protocol trigger condition. The injection protocol excludes the drip mode injection protocol—the drip mode injection protocol is not part of the injection protocol, or stated another way, the drip mode injection protocol is separate and distinct from the injection protocol.

A number of feature refinements and additional features are separately applicable to each of above-noted first, second, and third aspects of the present invention as well. These feature refinements and additional features may be used individually or in any combination in relation to each of the first, second, and third aspects. The power injector control logic may be of any appropriate form and/or configuration, may be implemented or integrated in an appropriate manner, or both (e.g., in the power injector software; implemented by software, hardware, firmware, and any combination thereof). In one embodiment, the functionality of the power injector control logic is provided by one or more processors of any appropriate size, shape, configuration, and/or type. In one embodiment, the functionality of the power injector control logic is provided by one or more computers. The power injector control logic may be operatively interconnected with one or more data entry devices of any appropriate configuration and/or type (e.g., a keyboard, a mouse, a touch screen display, a soft key display, a touch pad, a track ball, or the like) to facilitate interaction and control by an operator (e.g., a medical technician).

The injection protocol and drip mode injection protocol may be mutually exclusive. For instance, the power injector control logic may be configured such that the drip mode injection protocol is not simply part of the injection protocol. In one embodiment, the power injector control logic is configured such that only one of the injection protocol and the drip mode injection protocol is operating or controlling the operation of the power injector at any one time.

The injection protocol may include a first programmed sequence to control the manner in which one or more fluids are being delivered to a fluid target, such as by being injected into a patient. The injection protocol may be configured in any appropriate manner, may be input, selected, or retrieved in any appropriate manner, or both. A particular injection protocol may be configured to deliver a programmed volume of a first fluid at a first programmed flow rate, as well as a programmed volume of a second fluid at a second programmed flow rate. Each delivery of each of the first and second fluids may be characterized as a phase. One or more configurable phases may be utilized for each of the first and second fluids. In one embodiment, the first fluid is contrast media and the second fluid is saline. More generally, the injection protocol may be configured to use any appropriate number of fluids (including a single fluid or multiple fluids) and any appropriate number of phases (including a single phase or multiple phases), where each phase may be configured to deliver a predetermined fluid volume in a predetermined manner.

The drip mode injection protocol may be of any appropriate configuration. In one embodiment, the drip mode injection protocol may provide a drip injection—a low flow rate injection of a small volume of saline delivered to the patient to keep open the fluid pathway from the power injector to the patient. Any appropriate fluid may be utilized by the drip mode injection protocol, each such fluid may be delivered in any appropriate manner, or both for purposes of the drip mode injection protocol. In one embodiment, the flow rate for the drip injection is within a range at least generally from about 0.1 milliliters/second to at least generally about 1.0 milliliters/second. In one embodiment, the total volume of fluid delivered by a drip injection is within a range of at least generally about 0.1 milliliters to at least generally about 3.0 milliliters.

The power injector may include a graphical user interface (GUI) that allows an operator to configure one or both of the injection protocol and the drip mode injection protocol. The GUI may include one or more data entry devices of any appropriate configuration and/or type (e.g., a keyboard, a mouse, a touch screen display, a soft key display, a touch pad, a track ball, or the like) to facilitate interaction and control by an operator (e.g., a medical technician). In practice, an operator may use the GUI to configure various parameters including flow rate, flow duration, type of fluid, or the like. The drip mode injection protocol may be configurable before or after a suspension of the injection protocol. Further, in one embodiment, the drip mode injection protocol is hard-coded in memory of the power injector.

There are numerous ways in which the drip mode injection protocol may be initiated upon a suspension of the injection protocol. In one embodiment, the drip mode injection protocol is automatically initiated upon or immediately following an initiation or start of a suspension of the injection protocol. "Automatic" means that no operator interaction is required to initiate the drip mode injection protocol in this instance. In another embodiment, the drip mode injection protocol is automatically initiated after a predetermined delay following an initiation or start of a suspension of the injection protocol. For instance, if a suspension condition is identified in relation to the injection protocol, and if the suspended status continues for a certain amount of time, the drip mode injection protocol may be initiated. In yet another embodiment, the drip mode injection protocol is manually initiated following an occurrence of a suspension of the injection protocol. In this latter embodiment, the GUI may include a prompt to initiate the drip mode injection protocol.

The power injector control logic may be configured to transfer control from the injection protocol to the drip mode injection protocol. This "transfer of control" is subject to a number of characterizations. One is that control is transferred from the injection protocol to the drip mode injection protocol based at least in part upon a suspension of the injection protocol. Another is that the power injector control logic is configured to include a logic operator for transferring control from the injection protocol to the drip mode injection protocol. In one embodiment, this logic operator involves a determination as to whether the injection protocol has been suspended. Yet another is that the power injector control logic is configured to include a "trigger condition." In one embodiment, the "trigger condition" involves a suspension of the injection protocol. A suspension of the injection protocol may be determined in any appropriate manner. Moreover, and with regard to each of the logic operator and trigger condition embodiments, a suspension of the injection protocol alone may be used to initiate a drip mode injection protocol, or both a suspension and a continuation of a suspended status for a certain amount of time may be required to initiate the drip mode injection protocol.

A fourth aspect of the present invention is embodied by a method of operation for a power injector. The method includes executing an injection protocol that includes a first predetermined sequence, and thereafter suspending the injection protocol. The method further includes executing a drip mode injection at least some time after the injection protocol has been suspended, wherein the first predetermined sequence excludes the drip mode injection.

The various features discussed above with regard to one or more of the first through the third aspects may be utilized by the fourth aspect, including where the features of the drip mode injection protocol of the first through the third aspects are applicable to or control the drip mode injection of the fourth aspect, and further including without limitation: 1) regarding the configuration of and how each of the injection protocol and to the drip mode injection may be configured; and 2) how/when the drip mode injection may be initiated.

A number of feature refinements and additional features are separately applicable to each of above-noted first through fourth aspects of the present invention as well. These feature refinements and additional features may be used individually or in any combination in relation to each of the first through fourth aspects. Initially, any feature that is intended to be limited to a "singular" context or the like will be clearly set forth herein by terms such as "only," "single," "limited to," or the like. Merely introducing a feature in accordance with commonly accepted antecedent basis practice (or failing to not specify "at least one" in relation to a given feature) does not limit the corresponding feature to the singular (e.g., indicating that a power injector includes "a syringe" alone does not mean that the power injector includes only a single syringe).

Any "logic" that may be utilized by any of the various aspects of the present invention may be implemented in any appropriate manner, including without limitation in any appropriate software, firmware, or hardware, using one or more platforms, using one or more processors, using memory of any appropriate type, using any single computer of any appropriate type or a multiple computers of any appropriate type and interconnected in any appropriate manner, or any combination thereof. This logic may be implemented at any single location or at multiple locations that are interconnected in any appropriate manner (e.g., via any type of network).

The power injector may be of any appropriate size, shape, configuration, and/or type. The power injector may utilize one or more syringe plunger drivers of any appropriate size, shape, configuration, and/or type, where each such syringe plunger driver is capable of at least bi-directional movement (e.g., a movement in a first direction for discharging fluid; a movement in a second direction for accommodating a loading of fluid or so as to return to a position for a subsequent fluid discharge operation), and where each such syringe plunger driver may interact with its corresponding syringe plunger in any appropriate manner (e.g., by mechanical contact; by an appropriate coupling (mechanical or otherwise)) so as to be able to advance the syringe plunger in at least one direction (e.g., to discharge fluid). Each syringe plunger driver may utilize one or more drive sources of any appropriate size, shape, configuration, and/or type. Multiple drive source outputs may be combined in any appropriate manner to advance a single syringe plunger at a given time. One or more drive sources may be dedicated to a single syringe plunger driver, one or more drive sources may be associated with multiple syringe plunger drivers (e.g., incorporating a transmission of sorts to change the output from one syringe plunger to another syringe plunger), or a combination thereof. Representative drive source forms include a brushed or brushless electric motor, a hydraulic motor, a pneumatic motor, a piezoelectric motor, or a stepper motor.

The power injector may be used for any appropriate application where the delivery of one or more medical fluids is desired, including without limitation any appropriate medical application (e.g., computed tomography or CT imaging; magnetic resonance imaging or MRI; single photon emission computed tomography or SPECT imaging; positron emission tomography or PET imaging; X-ray imaging; angiographic imaging; optical imaging; ultrasound imaging). The power injector may be used in conjunction with any component or combination of components, such as an appropriate imaging system (e.g., a CT scanner). For instance, information could be conveyed between any such power injector and one or more other components (e.g., scan delay information, injection start signal, injection rate).

Any appropriate number of syringes may be utilized with the power injector in any appropriate manner (e.g., detachably; front-loaded; rear-loaded; side-loaded), any appropriate medical fluid may be discharged from a given syringe of any such power injector (e.g., contrast media, a radiopharmaceutical, saline, and any combination thereof), and any appropriate fluid may be discharged from a multiple syringe power injector configuration in any appropriate manner (e.g., sequentially, simultaneously), or any combination thereof. In one embodiment, fluid discharged from a syringe by operation of the power injector is directed into a conduit (e.g., a medical tubing set), where this conduit is fluidly interconnected with the syringe in any appropriate manner and directs fluid to a desired location (e.g., to a catheter that is inserted into a patient, for instance for injection). Multiple syringes may discharge into a common conduit (e.g., for provision to a single injection site), or one syringe may discharge into one conduit (e.g., for provision to one injection site), while another syringe may discharge into a different conduit (e.g., for provision to a different injection site). In one embodiment, each syringe includes a syringe barrel and a plunger that is disposed within and movable relative to the syringe barrel. This plunger may interface with the power injector's syringe plunger drive assembly such that the syringe plunger drive assembly is able to advance the plunger in at least one direction, and possibly in two different, opposite directions.

DETAILED DESCRIPTION

Figure 1:
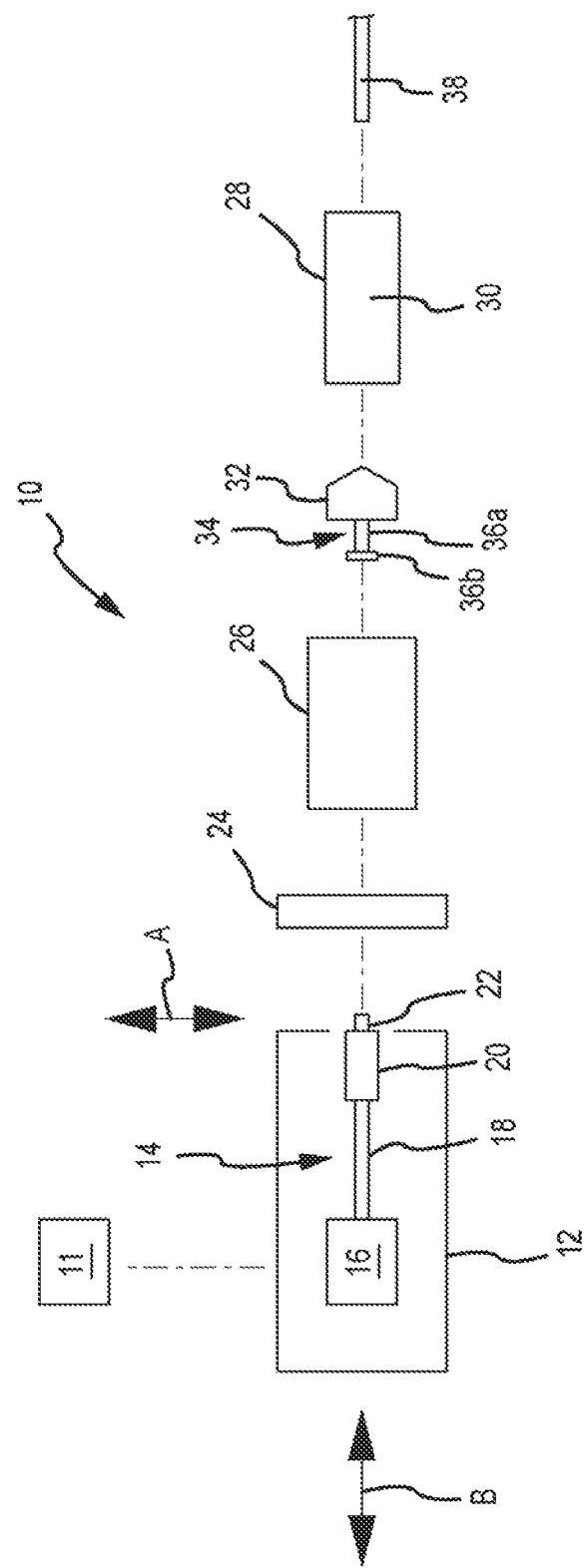
FIG. 1 is a schematic of one embodiment of a power injector.

FIG. 1 presents a schematic of one embodiment of a power injector 10 having a powerhead 12. One or more graphical user interfaces or GUIs 11 may be associated with the powerhead 12. Each GUI 11: 1) may be of any appropriate size, shape, configuration, and/or type; 2) may be operatively interconnected with the powerhead 12 in any appropriate manner; 3) may be disposed at any appropriate location; 4) may be configured to provide one or any combination of the following functions: controlling one or more aspects of the operation of the power injector 10; inputting/editing one or more parameters associated with the operation of the power injector 10; and displaying appropriate information (e.g., associated with the operation of the power injector 10); or 5) any combination of the foregoing. Any appropriate number of GUIs 11 may be utilized. In one embodiment, the power injector 10 includes a GUI 11 that is incorporated by a console that is separate from but which communicates with the powerhead 12. In another embodiment, the power injector 10 includes a GUI 11 that is part of the powerhead 12. In yet another embodiment, the power injector 10 utilizes one GUI 11 on a separate console that communicates with the powerhead 12, and also utilizes another GUI 11 that is on the powerhead 12. Each GUI 11 could provide the same functionality or set of functionalities, or the GUIs 11 may differ in at least some respect in relation to their respective functionalities.

A syringe 28 may be installed on this powerhead 12 and, when installed, may be considered to be part of the power injector 10. Some injection procedures may result in a relatively high pressure being generated within the syringe 28. In this regard, it may be desirable to dispose the syringe 28 within a pressure jacket 26. The pressure jacket 26 is typically associated with the powerhead 12 in a manner that allows the syringe 28 to be disposed therein as a part of or after installing the syringe 28 on the powerhead 12. The same pressure jacket 26 will typically remain associated with the powerhead 12, as various syringes 28 are positioned within and removed from the pressure jacket 26 for multiple injection procedures. The power injector 10 may eliminate the pressure jacket 26 if the power injector 10 is configured/utilized for low-pressure injections and/or if the syringe(s) 28 to be utilized with the power injector 10 is (are) of sufficient durability to withstand high-pressure injections without the additional support provided by a pressure jacket 26. In any case, fluid discharged from the syringe 28 may be directed into a conduit 38 of any appropriate size, shape, configuration, and/or type, which may be fluidly interconnected with the syringe 28 in any appropriate manner, and which may direct fluid to any appropriate location (e.g., to a patient).

The powerhead 12 includes a syringe plunger drive assembly or syringe plunger driver 14 that interacts (e.g., interfaces) with the syringe 28 (e.g., a plunger 32 thereof) to discharge fluid from the syringe 28. This syringe plunger drive assembly 14 includes a drive source 16 (e.g., a motor of any appropriate size, shape, configuration, and/or type, optional gearing, and the like) that powers a drive output 18 (e.g., a rotatable drive screw). A ram 20 may be advanced along an appropriate path (e.g., axial) by the drive output 18. The ram 20 may include a coupler 22 for interacting or interfacing with a corresponding portion of the syringe 28 in a manner that will be discussed below.

The syringe 28 includes a plunger or piston 32 that is movably disposed within a syringe barrel 30 (e.g., for axial reciprocation along an axis coinciding with the double-headed arrow B). The plunger 32 may include a coupler 34. This syringe plunger coupler 34 may interact or interface with the ram coupler 22 to allow the syringe plunger drive assembly 14 to retract the syringe plunger 32 within the syringe barrel 30. The syringe plunger coupler 34 may be in the form of a shaft 36a that extends from a body of the syringe plunger 32, together with a head or button 36b. However, the syringe plunger coupler 34 may be of any appropriate size, shape, configuration, and/or type.

Generally, the syringe plunger drive assembly 14 of the power injector 10 may interact with the syringe plunger 32 of the syringe 28 in any appropriate manner (e.g., by mechanical contact; by an appropriate coupling (mechanical or otherwise)) so as to be able to move or advance the syringe plunger 32 (relative to the syringe barrel 30) in at least one direction (e.g., to discharge fluid from the corresponding syringe 28). That is, although the syringe plunger drive assembly 14 may be capable of bi-directional motion (e.g., via operation of the same drive source 16), the power injector 10 may be configured such that the operation of the syringe plunger drive assembly 14 actually only moves each syringe plunger 32 being used by the power injector 10 in only one direction. However, the syringe plunger drive assembly 14 may be configured to interact with each syringe plunger 32 being used by the power injector 10 so as to be able to move each such syringe plunger 32 in each of two different directions (e.g. in different directions along a common axial path).

Retraction of the syringe plunger 32 may be utilized to accommodate a loading of fluid into the syringe barrel 30 for a subsequent injection or discharge, may be utilized to actually draw fluid into the syringe barrel 30 for a subsequent injection or discharge, or for any other appropriate purpose. Certain configurations may not require that the syringe plunger drive assembly 14 be able to retract the syringe plunger 32, in which case the ram coupler 22 and syringe plunger coupler 34 may not be desired. In this case, the syringe plunger drive assembly 14 may be retracted for purposes of executing another fluid delivery operation (e.g., after another pre-filled syringe 28 has been installed). Even when a ram coupler 22 and syringe plunger coupler 34 are utilized, it may such that these components may or may not be coupled when the ram 20 advances the syringe plunger 32 to discharge fluid from the syringe 28 (e.g., the ram 20 may simply "push on" the syringe plunger coupler 34 or on the syringe plunger 32). Any single motion or combination of motions in any appropriate dimension or combination of dimensions may be utilized to dispose the ram coupler 22 and syringe plunger coupler 34 in a coupled state or condition, to dispose the ram coupler 22 and syringe plunger coupler 34 in an un-coupled state or condition, or both.

The syringe 28 may be installed on the powerhead 12 in any appropriate manner. For instance, the syringe 28 could be configured to be installed directly on the powerhead 12. In the illustrated embodiment, a housing 24 is appropriately mounted on the powerhead 12 to provide an interface between the syringe 28 and the powerhead 12. This housing 24 may be in the form of an adapter to which one or more configurations of syringes 28 may be installed, and where at least one configuration for a syringe 28 could be installed directly on the powerhead 12 without using any such adapter. The housing 24 may also be in the form of a faceplate to which one or more configurations of syringes 28 may be installed. In this case, it may be such that a faceplate is required to install a syringe 28 on the powerhead 12—the syringe 28 could not be installed on the powerhead 12 without the faceplate. When a pressure jacket 26 is being used, it may be installed on the powerhead 12 in the various manners discussed herein in relation to the syringe 28, and the syringe 28 will then thereafter be installed in the pressure jacket 26.

The housing 24 may be mounted on and remain in a fixed position relative to the powerhead 12 when installing a syringe 28. Another option is to movably interconnect the housing 24 and the powerhead 12 to accommodate installing a syringe 28. For instance, the housing 24 may move within a plane that contains the double-headed arrow A to provide one or more of coupled state or condition and an un-coupled state or condition between the ram coupler 22 and the syringe plunger coupler 34.

Figure 2A:
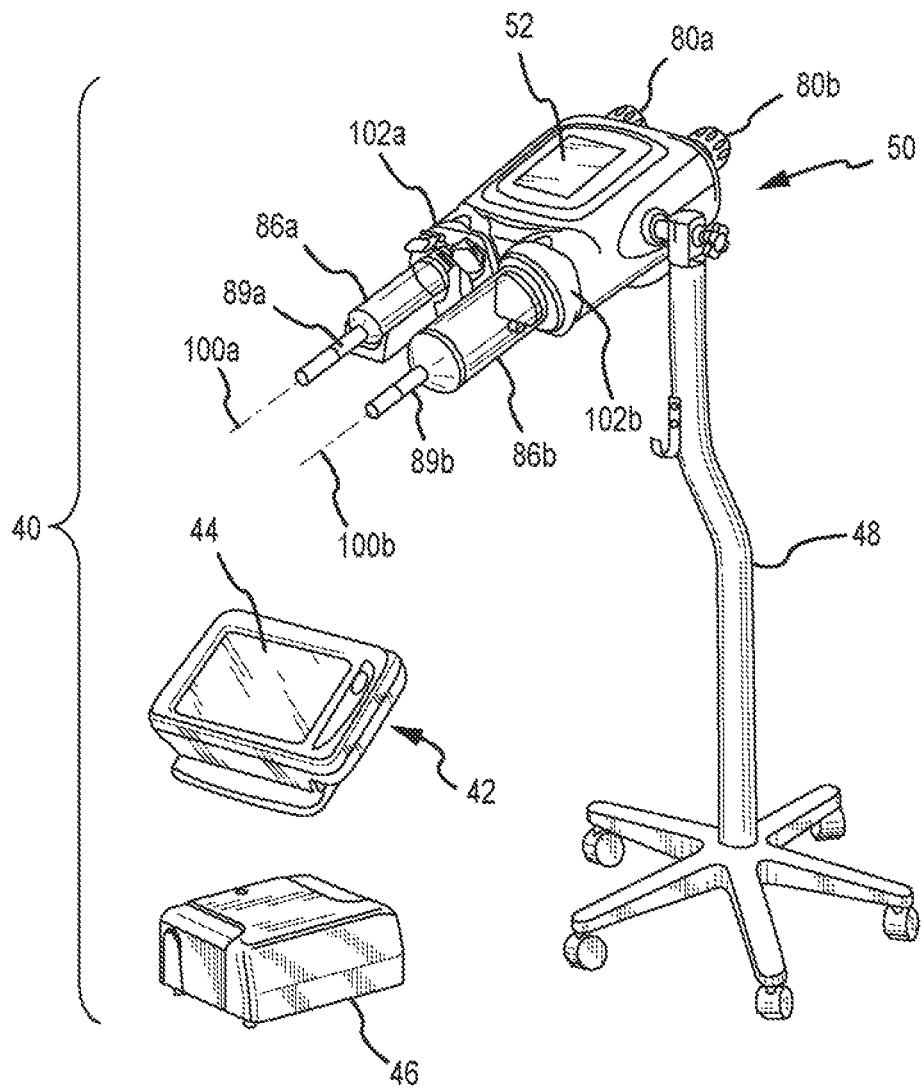
FIG. 2A is a perspective view of one embodiment of a portable stand-mounted, dual-head power injector.

One particular power injector configuration is illustrated in FIG. 2A, is identified by a reference numeral 40, and is at least generally in accordance with the power injector 10 of FIG. 1. The power injector 40 includes a powerhead 50 that is mounted on a portable stand 48. A pair of syringes 86a, 86b for the power injector 40 is mounted on the powerhead 50. Fluid may be discharged from the syringes 86a, 86b during operation of the power injector 40.

The portable stand 48 may be of any appropriate size, shape, configuration, and/or type. Wheels, rollers, casters, or the like may be utilized to make the stand 48 portable. The powerhead 50 could be maintained in a fixed position relative to the portable stand 48. However, it may be desirable to allow the position of the powerhead 50 to be adjustable relative to the portable stand 48 in at least some manner. For instance, it may be desirable to have the powerhead 50 in one position relative to the portable stand 48 when loading fluid into one or more of the syringes 86a, 86b, and to have the powerhead 50 in a different position relative to the portable stand 48 for performance of an injection procedure. In this regard, the powerhead 50 may be movably interconnected with the portable stand 48 in any appropriate manner (e.g., such that the powerhead 50 may be pivoted through at least a certain range of motion, and thereafter maintained in the desired position).

It should be appreciated that the powerhead 50 could be supported in any appropriate manner for providing fluid. For instance, instead of being mounted on a portable structure, the powerhead 50 could be interconnected with a support assembly, that in turn is mounted to an appropriate structure (e.g., ceiling, wall, floor). Any support assembly for the powerhead 50 may be positionally adjustable in at least some respect (e.g., by having one or more support sections that may be repositioned relative to one more other support sections), or may be maintained in a fixed position. Moreover, the powerhead 50 may be integrated with any such support assembly so as to either be maintained in a fixed position or so as to be adjustable relative the support assembly.

The powerhead 50 includes a graphical user interface or GUI 52. This GUI 52 may be configured to provide one or any combination of the following functions: controlling one or more aspects of the operation of the power injector 40; inputting/editing one or more parameters associated with the operation of the power injector 40; and displaying appropriate information (e.g., associated with the operation of the power injector 40). The power injector 40 may also include a console 42 and powerpack 46 that each may be in communication with the powerhead 50 in any appropriate manner (e.g., via one or more cables), that may be placed on a table or mounted on an electronics rack in an examination room or at any other appropriate location, or both. The powerpack 46 may include one or more of the following and in any appropriate combination: a power supply for the injector 40; interface circuitry for providing communication between the console 42 and powerhead 50; circuitry for permitting connection of the power injector 40 to remote units such as remote consoles, remote hand or foot control switches, or other original equipment manufacturer (OEM) remote control connections (e.g., to allow for the operation of power injector 40 to be synchronized with the x-ray exposure of an imaging system); and any other appropriate componentry. The console 42 may include a touch screen display 44, which in turn may provide one or more of the following functions and in any appropriate combination: allowing an operator to remotely control one or more aspects of the operation of the power injector 40; allowing an operator to enter/edit one or more parameters associated with the operation of the power injector 40; allowing an operator to specify and store programs for automated operation of the power injector 40 (which can later be automatically executed by the power injector 40 upon initiation by the operator); and displaying any appropriate information relation to the power injector 40 and including any aspect of its operation.

Figure 2B:
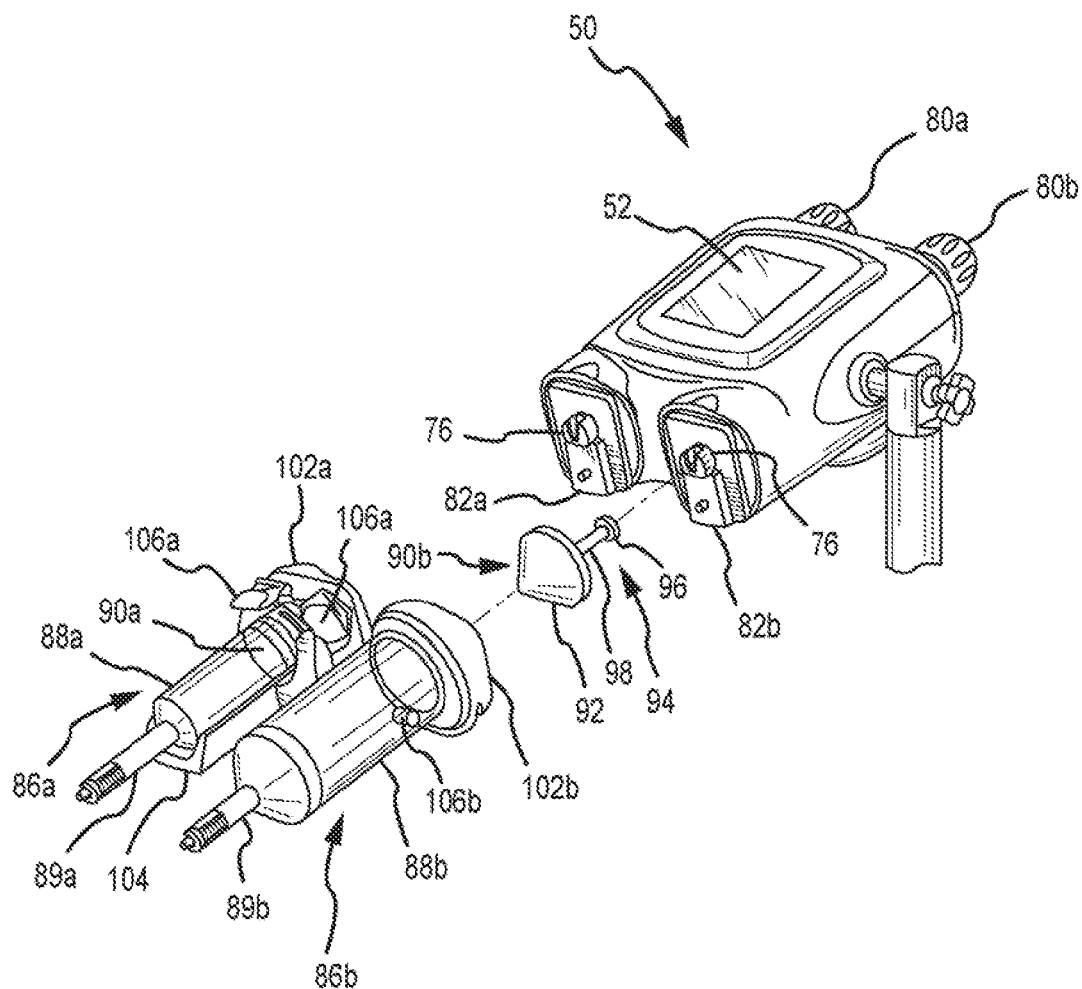
FIG. 2B is an enlarged, partially exploded, perspective view of a powerhead used by the power injector of FIG. 2A.

Various details regarding the integration of the syringes 86a, 86b with the powerhead 50 are presented in FIG. 2B. Each of the syringes 86a, 86b includes the same general components. The syringe 86a includes plunger or piston 90a that is movably disposed within a syringe barrel 88a. Movement of the plunger 90a along an axis 100a (FIG. 2A) via operation of the powerhead 50 will discharge fluid from within a syringe barrel 88a through a nozzle 89a of the syringe 86a. An appropriate conduit (not shown) will typically be fluidly interconnected with the nozzle 89a in any appropriate manner to direct fluid to a desired location (e.g., a patient). Similarly, the syringe 86b includes plunger or piston 90b that is movably disposed within a syringe barrel 88b. Movement of the plunger 90b along an axis 100b (FIG. 2A) via operation of the powerhead 50 will discharge fluid from within the syringe barrel 88b through a nozzle 89b of the syringe 86b. An appropriate conduit (not shown) will typically be fluidly interconnected with the nozzle 89b in any appropriate manner to direct fluid to a desired location (e.g., a patient).

The syringe 86a is interconnected with the powerhead 50 via an intermediate faceplate 102a. This faceplate 102a includes a cradle 104 that supports at least part of the syringe barrel 88a, and which may provide/accommodate any additional functionality or combination of functionalities. A mounting 82a is disposed on and is fixed relative to the powerhead 50 for interfacing with the faceplate 102a. A ram coupler 76 of a ram 74 (FIG. 2C), which are each part of a syringe plunger drive assembly or syringe plunger driver 56 (FIG. 2C) for the syringe 86a, is positioned in proximity to the faceplate 102a when mounted on the powerhead 50. Details regarding the syringe plunger drive assembly 56 will be discussed in more detail below in relation to FIG. 2C. Generally, the ram coupler 76 may be coupled with the syringe plunger 90a of the syringe 86a, and the ram coupler 76 and ram 74 (FIG. 2C) may then be moved relative to the powerhead 50 to move the syringe plunger 90a along the axis 100a (FIG. 2A). It may be such that the ram coupler 76 is engaged with, but not actually coupled to, the syringe plunger 90a when moving the syringe plunger 90a to discharge fluid through the nozzle 89a of the syringe 86a.

The faceplate 102a may be moved at least generally within a plane that is orthogonal to the axes 100a, 100b (associated with movement of the syringe plungers 90a, 90b, respectively, and illustrated in FIG. 2A), both to mount the faceplate 102a on and remove the faceplate 102a from its mounting 82a on the powerhead 50. The faceplate 102a may be used to couple the syringe plunger 90a with its corresponding ram coupler 76 on the powerhead 50. In this regard, the faceplate 102a includes a pair of handles 106a. Generally and with the syringe 86a being initially positioned within the faceplate 102a, the handles 106a may be moved to in turn move/translate the syringe 86a at least generally within a plane that is orthogonal to the axes 100a, 100b (associated with movement of the syringe plungers 90a, 90b, respectively, and illustrated in FIG. 2A). Moving the handles 106a to one position moves/translates the syringe 86a (relative to the faceplate 102a) in an at least generally downward direction to couple its syringe plunger 90a with its corresponding ram coupler 76. Moving the handles 106a to another position moves/translates the syringe 86a (relative to the faceplate 102a) in an at least generally upward direction to uncouple its syringe plunger 90a from its corresponding ram coupler 76.

The syringe 86b is interconnected with the powerhead 50 via an intermediate faceplate 102b. A mounting 82b is disposed on and is fixed relative to the powerhead 50 for interfacing with the faceplate 102b. A ram coupler 76 of a ram 74 (FIG. 2C), which are each part of a syringe plunger drive assembly 56 for the syringe 86b, is positioned in proximity to the faceplate 102b when mounted to the powerhead 50. Details regarding the syringe plunger drive assembly 56 again will be discussed in more detail below in relation to FIG. 20. Generally, the ram coupler 76 may be coupled with the syringe plunger 90b of the syringe 86b, and the ram coupler 76 and ram 74 (FIG. 2C) may be moved relative to the powerhead 50 to move the syringe plunger 90b along the axis 100b (FIG. 2A). It may be such that the ram coupler 76 is engaged with, but not actually coupled to, the syringe plunger 90b when moving the syringe plunger 90b to discharge fluid through the nozzle 89b of the syringe 86b.

The faceplate 102b may be moved at least generally within a plane that is orthogonal to the axes 100a, 100b (associated with movement of the syringe plungers 90a, 90b, respectively, and illustrated in FIG. 2A), both to mount the faceplate 102b on and remove the faceplate 102b from its mounting 82b on the powerhead 50. The faceplate 102b also may be used to couple the syringe plunger 90b with its corresponding ram coupler 76 on the powerhead 50. In this regard, the faceplate 102b may include a handle 106b. Generally and with the syringe 86b being initially positioned within the faceplate 102b, the syringe 86b may be rotated along its long axis 100b (FIG. 2A) and relative to the faceplate 102b. This rotation may be realized by moving the handle 106b, by grasping and turning the syringe 86b, or both. In any case, this rotation moves/translates both the syringe 86b and the faceplate 102b at least generally within a plane that is orthogonal to the axes 100a, 100b (associated with movement of the syringe plungers 90a, 90b, respectively, and illustrated in FIG. 2A). Rotating the syringe 86b in one direction moves/translates the syringe 86b and faceplate 102b in an at least generally downward direction to couple the syringe plunger 90b with its corresponding ram coupler 76. Rotating the syringe 86b in the opposite direction moves/translates the syringe 86b and faceplate 102b in an at least generally upward direction to uncouple its syringe plunger 90b from its corresponding ram coupler 76.

As illustrated in FIG. 2B, the syringe plunger 90b includes a plunger body 92 and a syringe plunger coupler 94. This syringe plunger coupler 94 includes a shaft 98 that extends from the plunger body 92, along with a head 96 that is spaced from the plunger body 92. Each of the ram couplers 76 includes a larger slot that is positioned behind a smaller slot on the face of the ram coupler 76. The head 96 of the syringe plunger coupler 94 may be positioned within the larger slot of the ram coupler 76, and the shaft 98 of the syringe plunger coupler 94 may extend through the smaller slot on the face of the ram coupler 76 when the syringe plunger 90b and its corresponding ram coupler 76 are in a coupled state or condition. The syringe plunger 90a may include a similar syringe plunger coupler 94 for interfacing with its corresponding ram coupler 76.

Figure 2C:
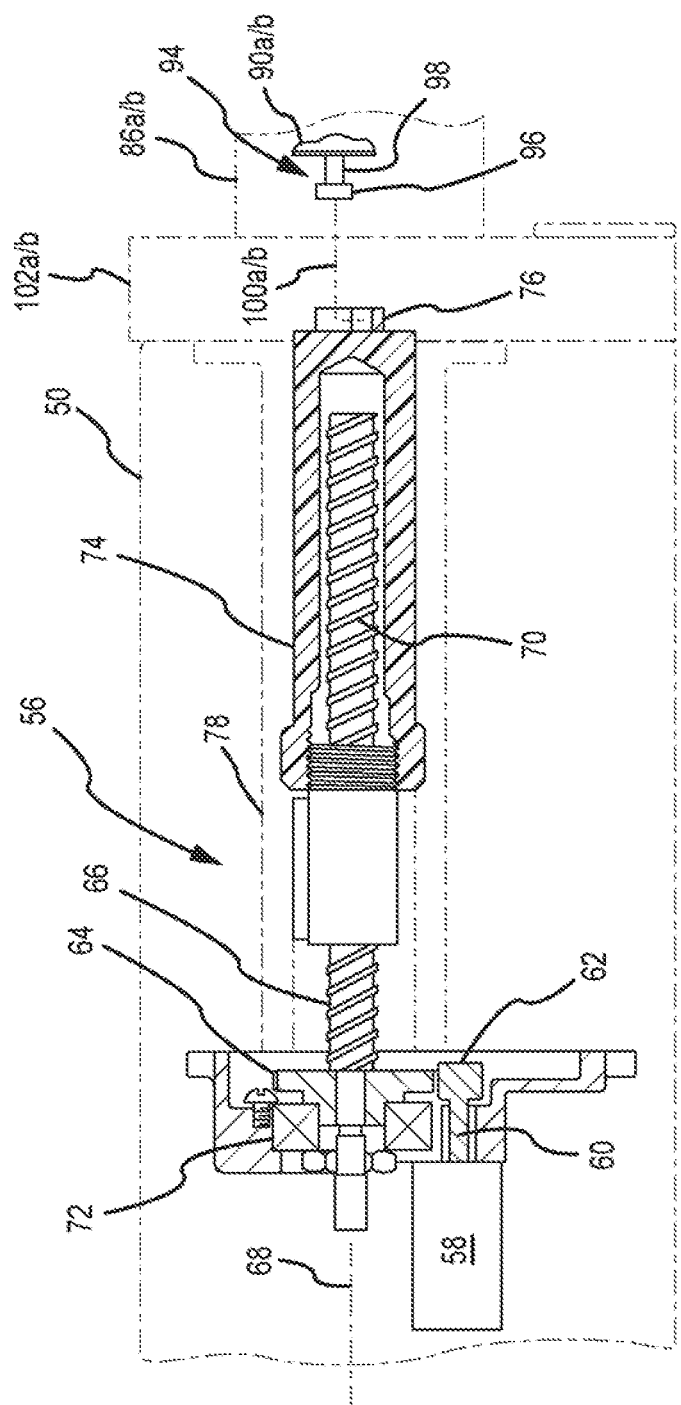
FIG. 2C is a schematic of one embodiment of a syringe plunger drive assembly used by the power injector of FIG. 2A.

The powerhead 50 is utilized to discharge fluid from the syringes 86a, 86b in the case of the power injector 40. That is, the powerhead 50 provides the motive force to discharge fluid from each of the syringes 86a, 86b. One embodiment of what may be characterized as a syringe plunger drive assembly or syringe plunger driver is illustrated in FIG. 2C, is identified by reference numeral 56, and may be utilized by the powerhead 50 to discharge fluid from each of the syringes 86a, 86b. A separate syringe plunger drive assembly 56 may be incorporated into the powerhead 50 for each of the syringes 86a, 86b. In this regard and referring back to FIGS. 2A-B, the powerhead 50 may include hand-operated knobs 80a and 80b for use in separately controlling each of the syringe plunger drive assemblies 56.

Initially and in relation to the syringe plunger drive assembly 56 of FIG. 2C, each of its individual components may be of any appropriate size, shape, configuration and/or type. The syringe plunger drive assembly 56 includes a motor 58, which has an output shaft 60. A drive gear 62 is mounted on and rotates with the output shaft 60 of the motor 58. The drive gear 62 is engaged or is at least engageable with a driven gear 64. This driven gear 64 is mounted on and rotates with a drive screw or shaft 66. The axis about which the drive screw 66 rotates is identified by reference numeral 68. One or more bearings 72 appropriately support the drive screw 66.

A carriage or ram 74 is movably mounted on the drive screw 66. Generally, rotation of the drive screw 66 in one direction axially advances the ram 74 along the drive screw 66 (and thereby along axis 68) in the direction of the corresponding syringe 86a/b, while rotation of the drive screw 66 in the opposite direction axially advances the ram 74 along the drive screw 66 (and thereby along axis 68) away from the corresponding syringe 86a/b. In this regard, the perimeter of at least part of the drive screw 66 includes helical threads 70 that interface with at least part of the ram 74. The ram 74 is also movably mounted within an appropriate bushing 78 that does not allow the ram 74 to rotate during a rotation of the drive screw 66. Therefore, the rotation of the drive screw 66 provides for an axial movement of the ram 74 in a direction determined by the rotational direction of the drive screw 66.

The ram 74 includes a coupler 76 that that may be detachably coupled with a syringe plunger coupler 94 of the syringe plunger 90a/b of the corresponding syringe 86a/b. When the ram coupler 76 and syringe plunger coupler 94 are appropriately coupled, the syringe plunger 90a/b moves along with ram 74. FIG. 2C illustrates a configuration where the syringe 86a/b may be moved along its corresponding axis 100a/b without being coupled to the ram 74. When the syringe 86a/b is moved along its corresponding axis 100a/b such that the head 96 of its syringe plunger 90a/b is aligned with the ram coupler 76, but with the axes 68 still in the offset configuration of FIG. 2C, the syringe 86a/b may be translated within a plane that is orthogonal to the axis 68 along which the ram 74 moves. This establishes a coupled engagement between the ram coupler 76 and the syringe plunger coupler 96 in the above-noted manner.

The power injectors 10, 40 of FIGS. 1 and 2A-C each may be used for any appropriate application, including without limitation for medical imaging applications where fluid is injected into a subject (e.g., a patient). Representative medical imaging applications for the power injectors 10, 40 include without limitation computed tomography or CT imaging, magnetic resonance imaging or MRI, SPECT imaging, PET imaging, X-ray imaging, angiographic imaging, optical imaging, and ultrasound imaging. The power injectors 10, 40 each could be used alone or in combination with one or more other components. The power injectors 10, 40 each may be operatively interconnected with one or more components, for instance so that information may be conveyed between the power injector 10, 40 and one or more other components (e.g., scan delay information, injection start signal, injection rate).

Any number of syringes may be utilized by each of the power injectors 10, 40, including without limitation single-head configurations (for a single syringe) and dual-head configurations (for two syringes). In the case of a multiple syringe configuration, each power injector 10, 40 may discharge fluid from the various syringes in any appropriate manner and according to any timing sequence (e.g., sequential discharges from two or more syringes, simultaneous discharges from two or more syringes, or any combination thereof). Multiple syringes may discharge into a common conduit (e.g., for provision to a single injection site), or one syringe may discharge into one conduit (e.g., for provision to one injection site), while another syringe may discharge into a different conduit (e.g., for provision to a different injection site). Each such syringe utilized by each of the power injectors 10, 40 may include any appropriate fluid (e.g., a medical fluid), for instance contrast media, a radiopharmaceutical, saline, and any combination thereof. Each such syringe utilized by each of the power injectors 10, 40 may be installed in any appropriate manner (e.g., rear-loading configurations may be utilized; front-loading configurations may be utilized; side-loading configurations may be utilized).

Figure 3:
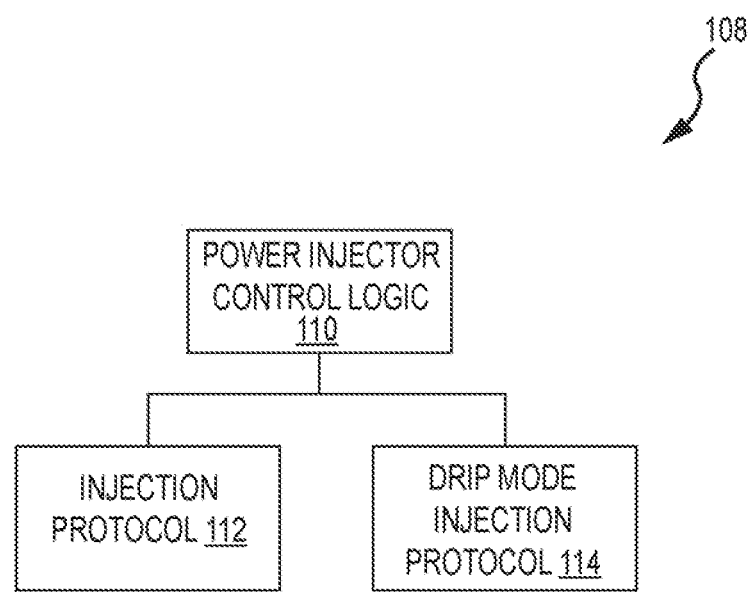
FIG. 3 is schematic of one embodiment of a power injector control system.

FIG. 3 illustrates one embodiment of a power injector control system 108 that may be utilized by any appropriate power injector, including without limitation the power injector 10 of FIG. 1 and the power injector 40 of FIGS. 2A-C. The power injector control system 108 may include a power injector control logic or module 110. The power injector control logic 110 may be of any appropriate form and/or configuration, may be implemented or integrated in an appropriate manner, or both (e.g., in the power injector software; implemented by software, hardware, firmware, and any combination thereof). In one embodiment, the functionality of the power injector control logic 110 is provided by one or more processors of any appropriate size, shape, configuration, and/or type. In one embodiment, the functionality of the power injector control logic 110 is provided by one or more computers. Further, the power injector control logic 110 may be operatively interconnected with one or more data entry devices of any appropriate configuration and/or type (e.g., a keyboard, a mouse, a touch screen display, a soft key display, a touch pad, a track ball, or the like) to facilitate interaction and control by an operator (e.g., a medical technician).

The power injector control logic 110 may be configured to include at least one fluid delivery or injection protocol 112 (e.g., for a medical application, and which may be referred to as a medical fluid delivery procedure or operation). The injection protocol 112 may be configured to control the manner in which one or more fluids are being delivered to a fluid target, such as by being injected into a patient. In one embodiment, the injection protocol 112 may be configured to deliver a programmed volume of a first fluid at a programmed flow rate, as well as a programmed volume of a second fluid at a programmed flow rate. Each delivery of each of the first and second fluids may be characterized as a phase. One or more phases may be utilized for each of the first and second fluids. In one embodiment, the first fluid is contrast media and the second fluid is saline or another appropriate flushing medium. Generally, the injection protocol 112 may be configured to use any appropriate number of fluids (including a single fluid or multiple fluids) and any appropriate number of phases (including a single phase or multiple phases), where each phase may deliver any appropriate fluid volume at any appropriate flow rate (including at one or more fixed flow rates, at one or more variable flow rates, or any combination thereof).

The power injector control logic 110 may include one or more additional protocols as desired/required, and which may be in the form of a programmed sequence. For example, the power injector control logic 110 may include a drip mode injection protocol 114. The drip mode injection protocol 114 may be configured to provide a drip injection—typically a low flow rate injection of a small volume of saline or other appropriate fluid delivered to the patient to keep open the fluid pathway from the power injector to the patient. In one embodiment, the flow rate for the drip injection is within a range at least generally from about 0.1 milliliters/second to at least generally about 1.0 milliliters/second, the total volume of fluid delivered by a drip injection is within a range of at least generally about 0.1 milliliters to at least generally about 3.0 milliliters, or both. In one embodiment, the flow rate for a drip injection may be adjusted by increments of 0.1 milliliters/second, the total fluid volume to be delivered by a drip injection may be adjusted by increments of 0.1 milliliters, or both.

In the illustrated embodiment, the injection protocol 112 and the drip mode injection protocol 114 are mutually exclusive—only one of the protocols 112, 114 is active or operating at any one time. When the power injector is being controlled by the injection protocol 112, it is not being controlled by the drip mode injection protocol 114. That is, the drip mode injection protocol 114 is not simply part of the injection protocol 112. Instead, the drip mode injection protocol 114 is initiated only during a suspension of the injection protocol 112. During this suspension, the power injector is being controlled by the drip mode injection protocol 114, not the injection protocol 112. The drip mode injection protocol 114 may be of any appropriate configuration, including using any appropriate fluid or combination of fluids, as well as using any appropriate flow rate (including one or more fixed flow rates, one or more variable flow rates, and any combination thereof).

Figure 4:
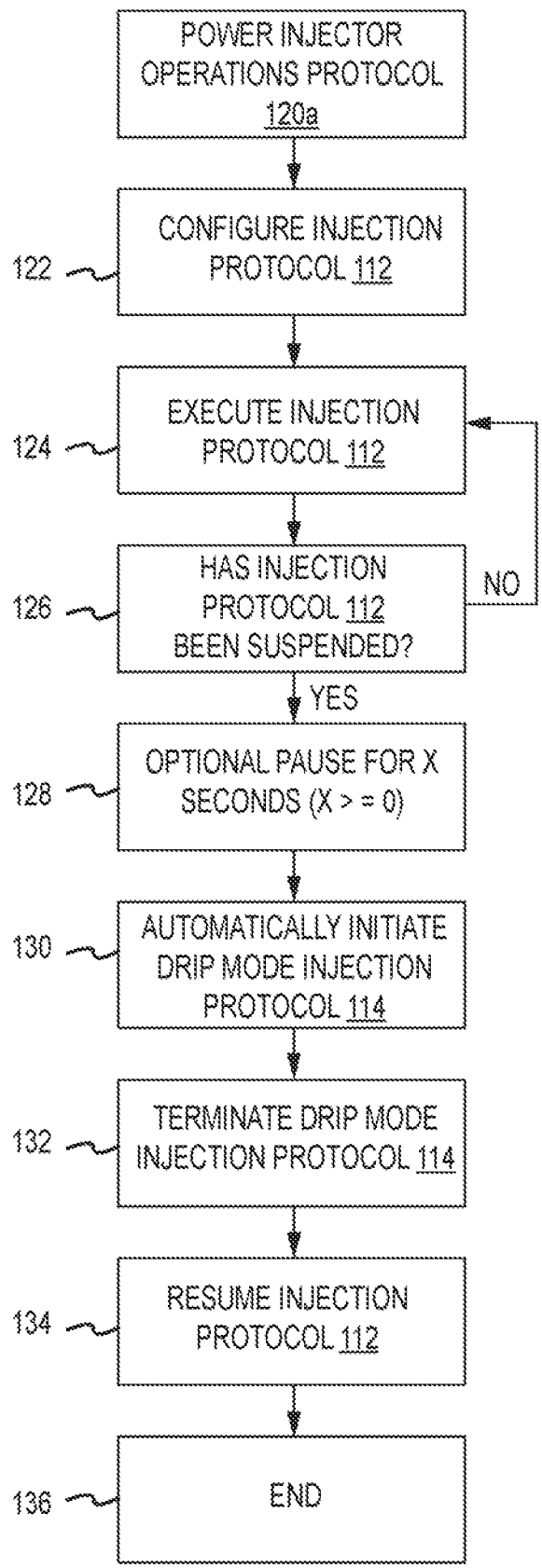
FIG. 4 is one embodiment of a power injector operations protocol that may be used by the power injector control system of FIG. 3.

FIGS. 4-8 illustrate various embodiments of power injector operations protocols 120*a-e*, with like reference numerals representing the same or similar steps. One embodiment of a power injector operations protocol 120*a* is illustrated in FIG. 4, and may be utilized by the power injector control logic 110 discussed above in relation to FIG. 3 to execute an injection protocol 112 and a drip mode injection protocol 114. Step 122 of the power injector operations protocol 120*a* is directed to configuring the injection protocol 112 in any appropriate manner and at any appropriate time. The injection protocol 112 may be input by operations personnel in any appropriate manner (e.g., via one or more data entry devices) or selected/retrieved in any appropriate manner (e.g., via one or more data entry devices), for instance, from a plurality of injection protocols 112 stored in memory and accessible through the power injector operations protocol 120*a*. A graphical user interface may be used to configure the injection protocol 112.

Step 124 of the power injector operations protocol 120*a* of FIG. 4 is directed to executing the injection protocol 112 that was configured in step 122. Step 126 is directed to determining if the injection protocol 112 has been suspended. Any way of determining if the injection protocol 112 has been suspended may be utilized for purposes of step 126. Suspension of the injection protocol 112 may be desirable for numerous reasons. For example, the injection protocol 112 may be suspended so that the position of a patient may be adjusted. Additionally or alternatively, the injection protocol 112 may be suspended to permit an operator (e.g., a medical technician) to perform other tasks such as configuring an imaging device, measuring one or more vital signs of a patient, or the like. The injection protocol 112 may be suspended manually, or automatically upon identifying an occurrence of one or more predefined conditions. Generally and for purposes of the power injector operations protocol 120*a*, any suspension associated with step 126 may be for any reason and may be initiated in any appropriate manner (e.g., manually, automatically). It should be appreciated that the injection protocol 112 may be completed without every having been suspended. In this regard, the power injector operations protocol 120*a* could include one or more additional steps in the "loop" between steps 124 and 126 to accommodate such a situation (not shown).

The power injector operations protocol 120*a* is only able to execute the drip mode injection protocol 114 after the injection protocol 112 has been suspended. The power injector operations protocol 120*a* may be configured to automatically initiate a drip mode injection protocol at step 130 after the injection protocol 112 has been suspended. As discussed above, the drip mode injection protocol 114 may be configured to deliver an appropriate fluid to the patient to keep open the fluid pathway from the power injector to the patient. In the embodiment of FIG. 4, the parameters for the drip mode injection protocol 114 are pre-configured, or hard-coded, into the power injector control logic 110. In this regard, an operator of the power injector does not control the values for various parameters for the drip mode injection protocol 114, including drip rate, drip volume, or the like. As such, the parameters may be stored in hardware and/or software associated with the power injector control logic 110. Further, it should be appreciated that the drip mode injection protocol 114 parameters may be updatable, but are not generally accessed by an operator during ordinary daily use of the power injector. As shown in step 128, the power injection operations protocol 120a may include an optional pause for the period of time between the time the injection protocol 112 is suspended, and the automatic initiation of the drip mode injection protocol 114. This pause may be desirable because, among other reasons, it may not be necessary to execute the drip mode injection protocol 114 if the pause is a relatively short duration (e.g., a few minutes). As such, the drip mode injection protocol 114 of the power injector operations protocol 120a may be automatically initiated immediately after any suspension of the injection protocol 112 (step 126), or following the expiration of a predetermined amount of time after the injection protocol 112 has been suspended (step 126).

Steps 132 and 134 of the power injector operations protocol 120a are directed to terminating the drip mode injection protocol 114 and resuming the injection protocol 112, respectively. These steps may be executed in any appropriate manner, including automatically or manually. In one embodiment, an operator may direct the power injector operations protocol 120a to terminate the drip mode injection protocol 114 and resume the injection protocol 112 by using a data entry device, such as a keyboard, a mouse, a touch screen display, a soft key display, a touch pad, a track ball, or the like. In another embodiment, the drip mode injection protocol 114 is executed for a definite period of time. After the drip mode injection protocol 114 has been terminated and the injection protocol 112 resumed, the operation protocol 120a may then continue until completion at step 136.

Figure 5:
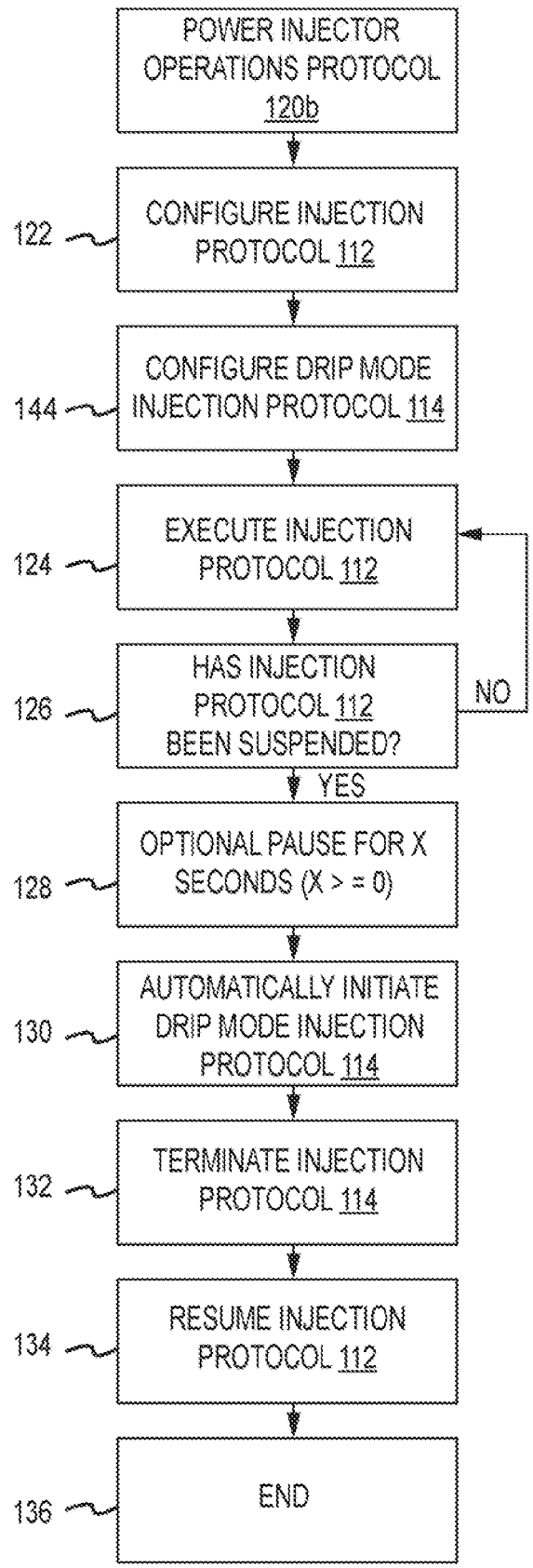
FIG. 5 is another embodiment of a power injector operations protocol that may be used by the power injector control system of FIG. 3.

Another embodiment of a power injector operations protocol 120b is illustrated in FIG. 5, and may be utilized by the power injector control logic 110 discussed above in relation to FIG. 3 to execute an injection protocol 112 and a drip mode injection protocol 114. In this embodiment, an operator may configure the drip mode injection protocol 114 pursuant to step 144. In this regard, an operator may use one or more data entry devices to input, retrieve, or select various parameters for the drip mode injection protocol 114, including drip rate, drip volume, duration of a pause prior to initiation of the drip mode injection protocol 114, or the like.

Similar to the power injector operations protocol 120a of FIG. 4, the power injector operations protocol 120b is configured to execute and identify a suspension of the injection protocol 112 in steps 124 and 126, respectively. Any way of determining if the injection protocol 112 has been suspended may be utilized for purposes of step 126. As in the case of the power injector operations protocol 120a of FIG. 4, it should be appreciated that the injection protocol 112 in the case of the power injector operations protocol 120b of FIG. 5 may be completed without every having been suspended. In this regard, the power injector operations protocol 120b could include one or more additional steps in the "loop" between steps 124 and 126 to accommodate such a situation (not shown).

The power injector operations protocol 120b of FIG. 5 is operable to automatically initiate the drip mode injection protocol 114 (step 130) after the injection protocol 112 (step 124) has been suspended. As shown, the protocol 120b may insert an optional pause between the suspension of the injection protocol 112 and the initiation of the drip mode injection protocol 114 (step 128). As discussed above, the duration for this pause may be input, retrieved, or selected by an operator in either of the configuration steps 122 and 144. Further, the operations protocol 120b is operable to terminate the drip mode injection protocol 114 (step 132), to resume the injection protocol 112 (step 134), and to end the operations protocol 120b at step 136.

Figure 6:
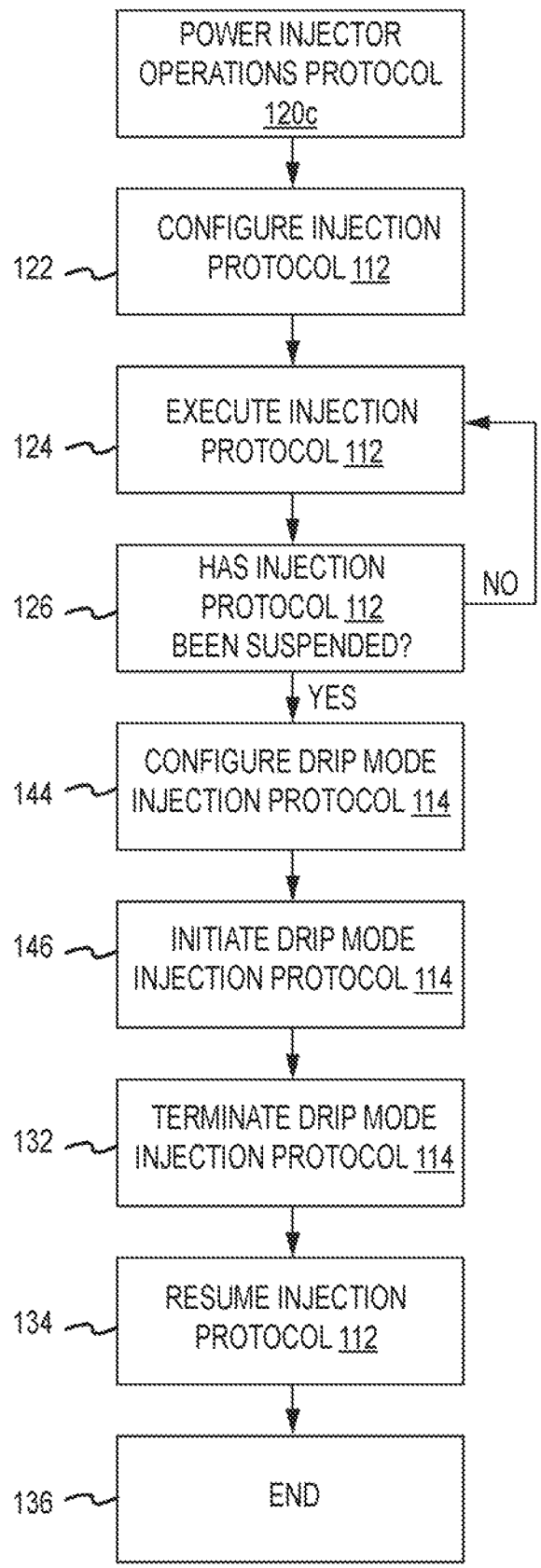
FIG. 6 is another embodiment of a power injector operations protocol that may be used by the power injector control system of FIG. 3.

Another embodiment of a power injector operations protocol 120c is illustrated in FIG. 6, and may be utilized by the power injector control logic 110 discussed above in relation to FIG. 3 to execute the injection protocol 112 and the drip mode injection protocol 114. Similar to previously described power injector operations protocols, the power injector operations protocol 120c is operable to configure the injection protocol 112 in step 122 in any appropriate manner and at any appropriate time. The operations protocol 120c may further be operable to execute and identify a suspension of the injection protocol 112 in steps 124 and 126, respectively. The manner in which the operations protocol 120c performs the aforementioned steps is described above with reference to the operations protocols 120a and 120b of FIGS. 4 and 5. As in the case of the power injector operations protocol 120a of FIG. 4, it should be appreciated that the injection protocol 112 in the case of the power injector operations protocol 120c of FIG. 6 may be completed without every having been suspended. In this regard, the power injector operations protocol 120c could include one or more additional steps in the "loop" between steps 124 and 126 to accommodate such a situation (not shown).

In the embodiment of FIG. 6, step 144 is directed to allowing an operator to configure the drip mode injection protocol 114 after the injection protocol 112 has been suspended. In this regard, the operations protocol 120c may provide an operator with the ability to input, retrieve, or select various parameters for the drip mode injection protocol 114 after the injection protocol 112 has been suspended in step 126. This may be accomplished in any suitable manner. For example, a display of the power injector may prompt the operator to use one or more data entry devices to input or select one or more parameters to define the drip mode injection protocol 114. The power injector operations protocol 120c described herein may be desirable because, among other reasons, an operator does not need to input or select the parameters for the drip mode injection protocol 114 until a time when the drip mode injection protocol 114 is to be executed.

Once an operator has configured the drip mode injection protocol 114, the power injector operations protocol 120c of FIG. 6 may initiate the drip mode injection protocol 114 in step 146. After the drip mode injection protocol 114 has been initiated, the power injector operations control protocol 120c may then terminate the drip mode injection protocol 114 (step 132). Further, the operations protocol 120c may then resume the injection protocol 112 (step 134), and finally terminate the injection sequence at step 136.

It should be appreciated that the drip mode injection protocol configuration step 144 may be executed in any particular order in the power injector operation protocols 120b and 120c. For example, in one embodiment, an operator may configure the drip mode injection protocol 114 after the start of and before the suspension of the injection protocol 112. Additionally or alternatively, an operator may configure the drip mode injection protocol 114 prior to the configuration of the injection protocol 112. Those skilled in the art will readily recognize that the power injector operations protocols 120b and 120c may provide flexibility in allowing an operator to configure the drip mode injection protocol 114. In this regard, a "default" drip mode injection protocol 114 may be pre-configured or hard-coded in any manner such that it is accessible by the power injector control logic 110, so that the drip mode injection protocol 114 may be executed even when an operator does not manually configure the same.

Figure 7:
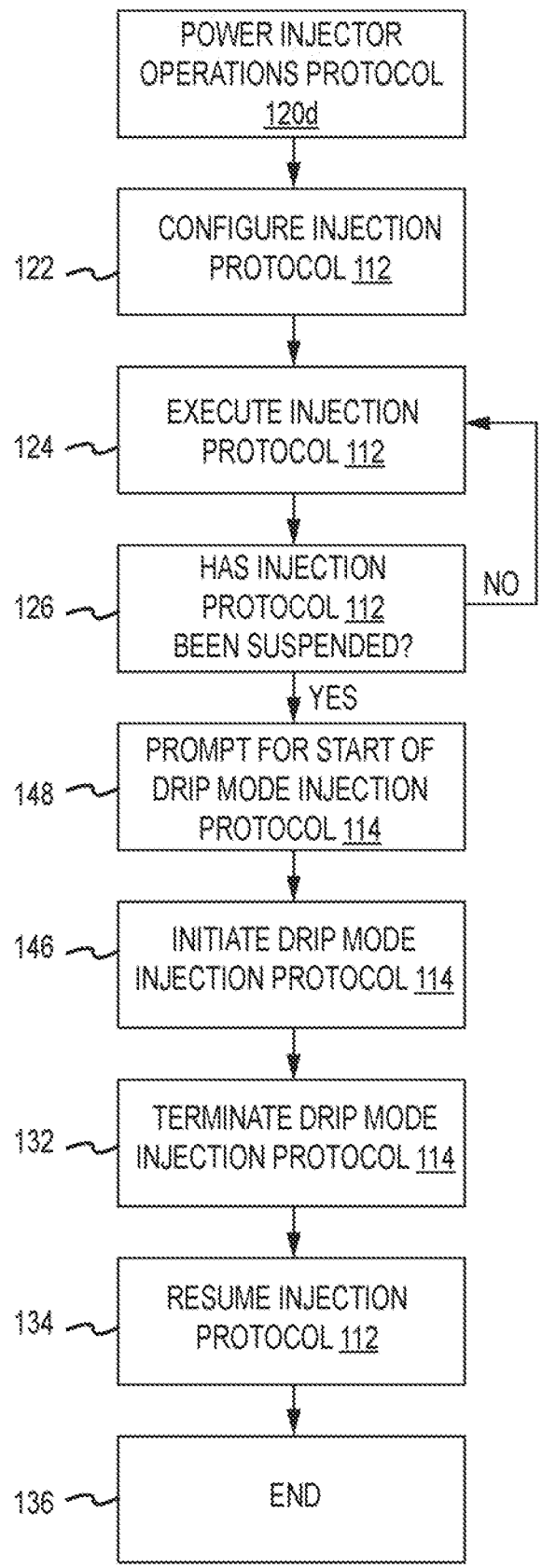
FIG. 7 is another embodiment of a power injector operations protocol that may be used by the power injector control system of FIG. 3.

FIG. 7 illustrates another embodiment of a power injector operations protocol 120d, and which may be utilized by the power injector control logic 110 discussed above in relation to FIG. 3 to execute an injection protocol 112 and a drip mode injection protocol 114. In this embodiment, an injection protocol 112 may be configured in step 122. Next, the injection protocol 112 may be executed in step 124, and then the operations protocol 120d may determine whether the injection protocol has been suspended in step 126. Once the injection protocol 112 has been suspended, the power injector operations protocol 120d may issue a prompt for an operator to initiate the start of the drip mode injection protocol 114 in step 148. The prompt may be issued in any suitable manner. For example, in one embodiment, a message on a display screen is provided that directs an operator to manipulate one or more data entry devices when they are ready to initiate the drip mode injection protocol 114. In another example, an audible signal may be utilized to notify an operator that action is required to initiate the drip mode injection protocol 114. It should be appreciated that various features described above and additional features may be combined in any suitable manner. For example, in one embodiment, the prompt may include a user interface to permit an operator to enter various configuration parameters for the subsequent drip mode injection protocol 114 prior to its initiation at step 146. In this regard, a "default" set of configuration parameters may be used if an operator fails to input or select one or more of the various parameters. Further, the prompt may be configured to initiate the drip mode injection protocol 114 (step 146) after a certain period of time has elapsed without any interaction by an operator. This feature may be useful in certain circumstances where, for whatever reason, an operator has failed to respond to the prompt to initiate the drip mode injection protocol 114.

After the drip mode injection protocol 114 has been initiated, the power injector operations control protocol 120d may then terminate the drip mode injection protocol 114 (step 132). Further, the operations protocol 120d may then resume the injection protocol 112 (step 134), and finally terminate the injection sequence at step 136. As in the case of the power injector operations protocol 120a of FIG. 4, it should be appreciated that the injection protocol 112 in the case of the power injector operations protocol 120d of FIG. 7 may be completed without every having been suspended. In this regard, the power injector operations protocol 120d could include one or more additional steps in the "loop" between steps 124 and 126 to accommodate such a situation (not shown).

Figure 8:
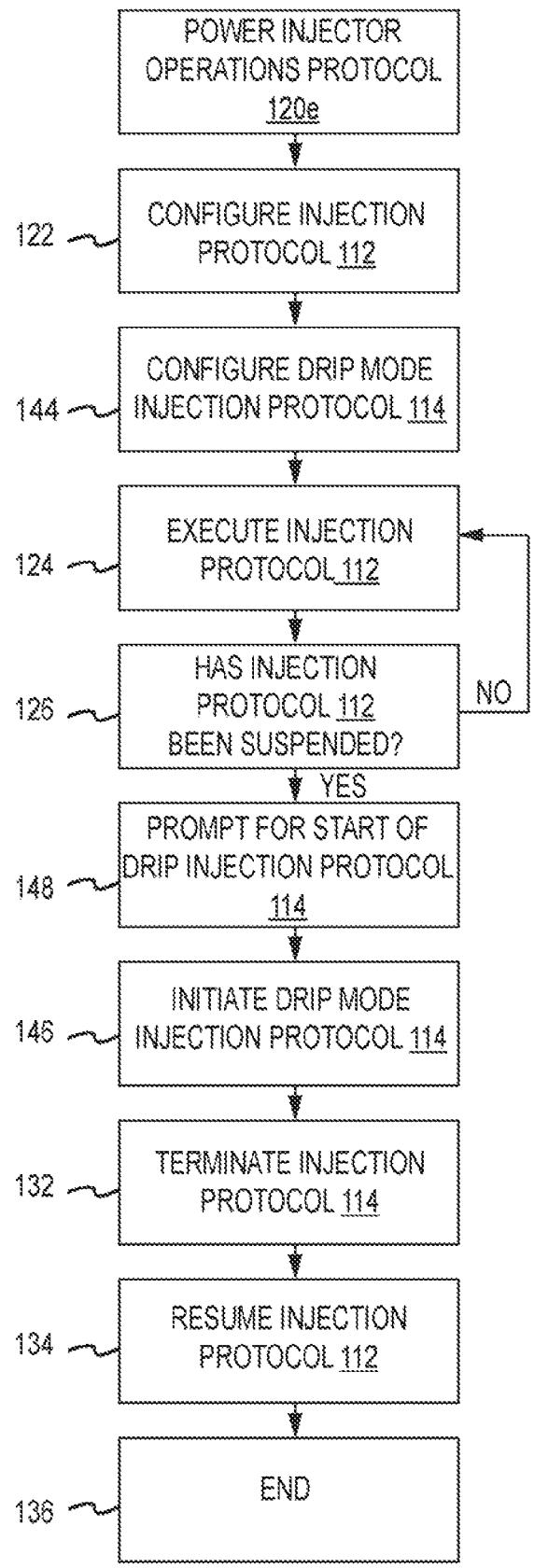
FIG. 8 is another embodiment of a power injector operations protocol that may be used by the power injector control system of FIG. 3.

FIG. 8 illustrates another embodiment of a power injector operations protocol 120e, and which may be utilized by the power injector control logic 110 discussed above in relation to FIG. 3 to execute an injection protocol 112 and a drip mode injection protocol 114. In this embodiment, the operations protocol 120e provides for the configuration of the injection protocol 112 and the drip mode injection protocol 114 in steps 122 and 144, respectively, prior to the execution of the injection protocol 112 in step 124. That is, the drip mode injection protocol 114 may be pre-programmed by the operator. Once it has been determined that the injection protocol 112 has been suspended (step 126), a prompt may be issued by the operations protocol 120e to initiate the drip mode injection protocol 114 (step 148). In this regard, the operator retains manual control over the initiation of the drip mode injection protocol 114, which may occur at step 146.

After the drip mode injection protocol 114 has been initiated, the power injector operations control protocol 120e may then terminate the drip mode injection protocol 114 (step 132). Further, the operations protocol 120e may then resume the injection protocol 112 (step 134), and finally terminate the injection sequence at step 136. As in the case of the power injector operations protocol 120a of FIG. 4, it should be appreciated that the injection protocol 112 in the case of the power injector operations protocol 120e of FIG. 8 may be completed without every having been suspended. In this regard, the power injector operations protocol 120e could include one or more additional steps in the "loop" between steps 124 and 126 to accommodate such a situation (not shown).

In summary, the power injector control logic 110 may be implemented in any appropriate manner, including without limitation in any appropriate software, firmware, or hardware, using one or more platforms, using one or more processors, using memory of any appropriate type, using any single computer of any appropriate type or a multiple computers of any appropriate type and interconnected in any appropriate manner, or both (e.g., in the power injector software; implemented by software, hardware, firmware, and any combination thereof). The power injector control logic 110 may be implemented at any single location or at multiple locations that are interconnected in any appropriate manner (e.g., via any type of network).

The power injector control logic 110 may be configured to handle a suspension of an injection protocol 112 in various manners in relation to a drip mode injection 114. The drip mode injection protocol 114 may be preconfigured, predetermined, or "hard-coded", and may be automatically initiated (power injector operations protocol 120a of FIG. 4) or may be manually initiated (power injector operations protocol 120d of FIG. 7). The drip mode injector protocol 114 may be configured prior to the start of an injection procedure, and may be automatically initiated (power injector operations protocol 120b of FIG. 5) or may be manually initiated (power injector operations protocol 120e of FIG. 8). Finally, the drip mode injector protocol 114 may be configured after an injection protocol 112 has been suspended, and then may be manually initiated (power injector operations protocol 120c of FIG. 6).

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed:

1. A power injector comprising:
   a syringe plunger driver comprising a motorized drive source;
   a first syringe comprising a first plunger;
   a first fluid in said first syringe, wherein said first fluid is contrast media;
   a second syringe comprising a second syringe plunger;
   a second fluid in said second syringe, wherein said second fluid is different from said first fluid; and
   power injector control logic comprising:
     an injection protocol, wherein said injection protocol comprises a first programmed sequence;

a drip mode injection protocol, wherein said drip mode injection protocol comprises a second programmed sequence that is not part of said first programmed sequence such that said injection protocol excludes said drip mode injection protocol, wherein said injection protocol and said drip mode injection protocol are mutually exclusive in that only one of said injection protocol and said drip mode injection protocol can control operation of said power injector at any one time, wherein said injection protocol consists of a set of phases that excludes said drip mode injection protocol, wherein each said phase of said injection protocol comprises a programmed volume of a specified fluid that is delivered at a programmed flow rate, wherein said set of phases for said injection protocol comprises first and second phases, wherein said first phase delivers said first fluid from said first syringe, wherein said second phase delivers said second fluid from said second syringe, and wherein said drip mode injection protocol is configured to deliver a low flow rate injection of a small volume of said second fluid from said second syringe to keep open fluid communication between said power injector and a patient;

a logic operator, wherein said logic operator is configured to transfer control from said injection protocol to said drip mode injection protocol upon an occurrence of and in response to a first condition, wherein said first condition comprises a suspension of said injection protocol that is identified by said power injector;

a graphical user interface; and a first prompt presented on said graphical user interface to initiate said drip mode injection protocol, wherein presentation of said first prompt is in response to an identified occurrence of said suspension of said injection protocol by said power injector, wherein said drip mode injection protocol is manually initiated by receipt of user input to said first prompt, wherein execution of said injection protocol resumes after termination of said drip mode injection protocol, and wherein said syringe plunger driver is operated: 1) to advance said first plunger of said first syringe in a fluid discharge direction for said first phase of said injection protocol; 2) to advance said second plunger of said second syringe in a fluid discharge direction for said second phase of said injection protocol; and 3) to advance said second plunger of said second syringe in said fluid discharge direction for said drip mode injection protocol.

2. A power injector comprising:

a syringe plunger driver comprising a motorized drive source;

a first syringe comprising a first plunger;

a first fluid in said first syringe, wherein said first fluid is contrast media;

a second syringe comprising a second syringe plunger;

a second fluid in said second syringe, wherein said second fluid is different from said first fluid; and power injector control logic comprising:

an injection protocol, wherein said injection protocol comprises a first programmed sequence;

a drip mode injection protocol, wherein said drip mode injection protocol comprises a second programmed sequence that is not part of said first programmed sequence such that said injection protocol excludes said drip mode injection protocol, wherein said injection protocol and said drip mode injection protocol are mutually exclusive in that only one of said injection protocol and said drip mode injection protocol can control operation of said power injector at any one time, wherein said injection protocol consists of a set of phases that excludes said drip mode injection protocol, wherein each said phase of said injection protocol comprises a programmed volume of a specified fluid that is delivered at a programmed flow rate, wherein said set of phases for said injection protocol comprises first and second phases, wherein said first phase delivers said first fluid from said first syringe, wherein said second phase delivers said second fluid from said second syringe, and wherein said drip mode injection protocol is configured to deliver a low flow rate injection of a small volume of said second fluid from said second syringe to keep open fluid communication between said power injector and a patient; and a drip mode injection protocol trigger condition, wherein said drip mode injection protocol trigger condition comprises a suspension of said injection protocol that is identified by said power injector, wherein satisfaction of said drip mode injection protocol trigger condition allows for execution of said drip mode injection protocol, wherein said drip mode injection protocol is automatically initiated after expiration of a predetermined delay following an identified occurrence of said suspension of said injection protocol by said power injector, wherein execution of said injection protocol resumes after termination of said drip mode injection protocol, and wherein said syringe plunger driver is operated: 1) to advance said first plunger of said first syringe in a fluid discharge direction for said first phase of said injection protocol; 2) to advance said second plunger of said second syringe in a fluid discharge direction for said second phase of said injection protocol; and 3) to advance said second plunger of said second syringe in said fluid discharge direction for said drip mode injection protocol.

3. The power injector of claim 2, wherein said injection protocol is configurable.

4. The power injector of claim 2, further comprising:

a graphical user interface, wherein at least one of said injection protocol and said drip mode injection protocol may be configured through said graphical user interface.

5. The power injector of claim 2, wherein said drip mode injection protocol is configurable after said suspension of said injection protocol.

6. The power injector of claim 2, wherein said drip mode injection protocol is hard-coded.

7. The power injector of claim 2, wherein said drip mode injection protocol is configurable prior to execution of said injection protocol.

8. A method of operation for a power injector comprising:

executing an injection protocol, wherein said injection protocol comprises a first programmed sequence, wherein said injection protocol consists of a set of phases that excludes a drip mode injection protocol, wherein each said phase of said injection protocol comprises a programmed volume of a specified fluid that is delivered at a programmed flow rate, wherein said set of phases for said injection protocol comprises first and second phases, wherein execution of said first phase comprises operating a syringe plunger driver of said power injector to advance a first plunger of a first syringe in a fluid discharge direction to discharge a first fluid out of said first syringe, wherein execution of said second phase comprises operating said syringe plunger driver of said power injector to advance a second plunger of a second syringe in a fluid discharge direction to discharge a second fluid out of said second syringe, wherein said second fluid is different from said first fluid, and wherein said first fluid is contrast media;

monitoring for a suspension of said injection protocol;

issuing a prompt to initiate said drip mode injection protocol in response to said suspension having been identified by said monitoring step, wherein said prompt is presented on a graphical user interface;

receiving user input in relation to said prompt; and executing said drip mode injection protocol in response to said user input, wherein said executing said drip mode injection protocol step comprises operating said syringe plunger driver of said power injector to advance said second plunger of said second syringe in said fluid discharge direction to discharge said second fluid out of said second syringe, wherein said drip mode injection protocol comprises a second programmed sequence that is not part of said first programmed sequence such that said injection protocol excludes said drip mode injection protocol, wherein said injection protocol and said drip mode injection protocol are mutually exclusive in that only one of said injection protocol and said drip mode injection protocol can control operation of said power injector at any one time, wherein said drip mode injection protocol is configured to deliver a low flow rate injection of a small volume of said second fluid out of said second syringe to keep open fluid communication between said power injector and a patient, and wherein said executing an injection protocol step, said monitoring step, said issuing a prompt step, said receiving step, and said executing said drip mode injection protocol step are all done by said power injector.

9. The method of claim 8, further comprising:
configuring said injection protocol prior to said executing an injection protocol step.

10. The method of claim 9, wherein said configuring said injection protocol step is executed through said graphical user interface.

11. The method of claim 8, further comprising:
configuring said drip mode injection protocol after said suspension is identified by said monitoring step.

12. The method of claim 11, wherein said configuring said drip mode injection protocol step is executed through said graphical user interface.

13. The method of claim 8, wherein said drip mode injection protocol is hard-coded.

14. The method of claim 8, further comprising:
configuring said drip mode injection protocol before said executing an injection protocol step.

15. The method of claim 14, wherein said configuring a drip mode injection protocol step is executed through said graphical user interface.

* * * * *